(12) United States Patent
Kronewitter et al.

(10) Patent No.: US 10,369,521 B2
(45) Date of Patent: Aug. 6, 2019

(54) SYSTEM AND METHOD FOR REAL-TIME ISOTOPE IDENTIFICATION

(71) Applicant: Thermo Finnigan LLC, San Jose, CA (US)

(72) Inventors: Scott R. Kronewitter, Waltham, MA (US); James L. Stephenson, Jr., Raleigh, NC (US); Ping F. Yip, Salem, MA (US)

(73) Assignee: THERMO FINNIGAN LLC, San Jose, CA (US)

( * ) Notice: Subject to any disclaimer, the term of this patent is extended or adjusted under 35 U.S.C. 154(b) by 0 days.

(21) Appl. No.: 15/725,422

(22) Filed: Oct. 5, 2017

(65) Prior Publication Data

US 2018/0099249 A1 Apr. 12, 2018

Related U.S. Application Data

(60) Provisional application No. 62/405,452, filed on Oct. 7, 2016.

(51) Int. Cl.
| | |
|---|---|
| *G01N 30/72* | (2006.01) |
| *H01J 49/00* | (2006.01) |
| *B01D 59/44* | (2006.01) |
| *G01N 30/86* | (2006.01) |
| *G01N 30/00* | (2006.01) |

(52) U.S. Cl.
CPC .............. *B01D 59/44* (2013.01); *G01N 30/72* (2013.01); *G01N 30/8613* (2013.01); *G01N 30/8631* (2013.01); *G01N 30/8675* (2013.01); *G01N 30/8693* (2013.01); *G01N 30/8696* (2013.01); *H01J 49/0036* (2013.01); *G01N 2030/77* (2013.01); *G01N 2030/862* (2013.01); *G01N 2223/302* (2013.01)

(58) Field of Classification Search
CPC .. G01N 2030/86; B01D 59/44; H01J 49/0036
See application file for complete search history.

(56) References Cited

U.S. PATENT DOCUMENTS

| 5,538,897 A | 7/1996 | Yates, III et al. |
| 9,074,236 B2 | 7/2015 | Stephenson, Jr. et al. |

(Continued)

OTHER PUBLICATIONS

Chen et al., "Automated Intensity Descent Algorithm for Interpretation of Complex High-Resolution Mass Spectra," Anal. Chem., 78, 5006-5018, 2006.

(Continued)

*Primary Examiner* — Eliza W Osenbaugh-Stewart
(74) *Attorney, Agent, or Firm* — Thermo Finnigan LLC; Gregory Kline

(57) ABSTRACT

An embodiment of a method for real time material identification is described that comprises determining an approximate mass value for an unknown material from spectral information derived from mass spectral analysis of the unknown material; retrieving profile models that correspond to a known material from a data structure using the approximate mass value; fitting a sample profile for the unknown material from the spectral information to the profile models to generate a fit score for each fit, wherein the lowest fit score corresponds to the best fit; calculating a mass value from the best fitting profile model and the sample profile.

44 Claims, 13 Drawing Sheets

(56) References Cited

U.S. PATENT DOCUMENTS

| | | | | |
|---|---|---|---|---|
| 2003/0099999 | A1* | 5/2003 | Wei | C12Q 1/6818 435/6.11 |
| 2007/0158542 | A1 | 7/2007 | Bauer et al. | |
| 2010/0171032 | A1* | 7/2010 | Wang | H01J 9/0009 250/282 |
| 2016/0268112 | A1 | 9/2016 | Yip et al. | |

OTHER PUBLICATIONS

Du et al., "Automatic Deconvolution of Isotope-Resolved Mass Spectra using Variable Selection and Quantized Peptide Mass Distribution," Anal. Chem., 78, 3385-3392, 2006.

Gras et al., "Improving protein identification from peptide mass fingerprinting through a parameterized multi-level scoring algorithm and an optimized peak detection," Electrophoresis, 20, 3535-3550, 1999.

Horn, et al., "Automated Reduction and Interpretation of High Resolution Electrospray Mass Spectra of Large Molecules,"J. Am. Soc. Mass Spectrom., vol. 11, No. 4., (2000), pp. 320-332.

Kronewitter et al., "The Glycolyzer: Automated Glycan Annotation Software for High Performance Mass Spectrometry and Its Application to Ovarian Cancer Glycan Biomarker Discovery," Proteomics, 12(15-16), 2523-2538, 2012.

Kronewitter et al., GlyQ-IQ: Glycomics Quintavariate-Informed Quantification with High-Performance Computing and GlycoGrid 4D Visualization, Anal. Chem., 2014, 6268-6276, 86(13).

Li et al., "A Software Suite for the Generation and Comparison of Peptide Arrays from Sets of Data Collected by Liquid Chromatography-Mass Spectrometry," Molecular & Cellular Proteomics 4.9, 13 pgs., 2005.

Li et al., Mono-isotope Prediction for Mass Spectra Using Bayes Network, Tsinghua Sci Technol, 19(6), 617-623, 2014.

Renard et al., "NITPICK: peak identification for mass spectrometry data", BMC Bioinformatics 2008, 9, 355, pp. 1-16.

Samuelsson et al., "Modular, scriptable and automated analysis tools for high-throughput peptide mass fingerprinting," Bioinformatics, 20(18), 3628-3635, 2004.

Senko et al., "Determination of monoisotopic masses and ion populations for large biomolecules from resolved isotopicdistributions," Journal of the American Society of Mass Spectrometry, 1995, vol. 6, pp. 229-233.

Wehofsky et al., "Automated deconvolution and deisotoping of electrospray mass spectra," J. of Mass Spectrometry, 37, 223-229, 2002.

Zhang et al., "A Universal Algorithm for Fast and Automated Charge State Deconvolution of Electrospray Mass-to-Charge Ratio Spectra", J Am Soc Mass Spectrom 1998, 9, pp. 225 233.

Valkenborg et al., "A Model-Based Method for the Prediction of the Isotopic Distribution of Peptides," Amer. Soc. of Mass Spec., 19(5), 703-712, 2008.

\* cited by examiner

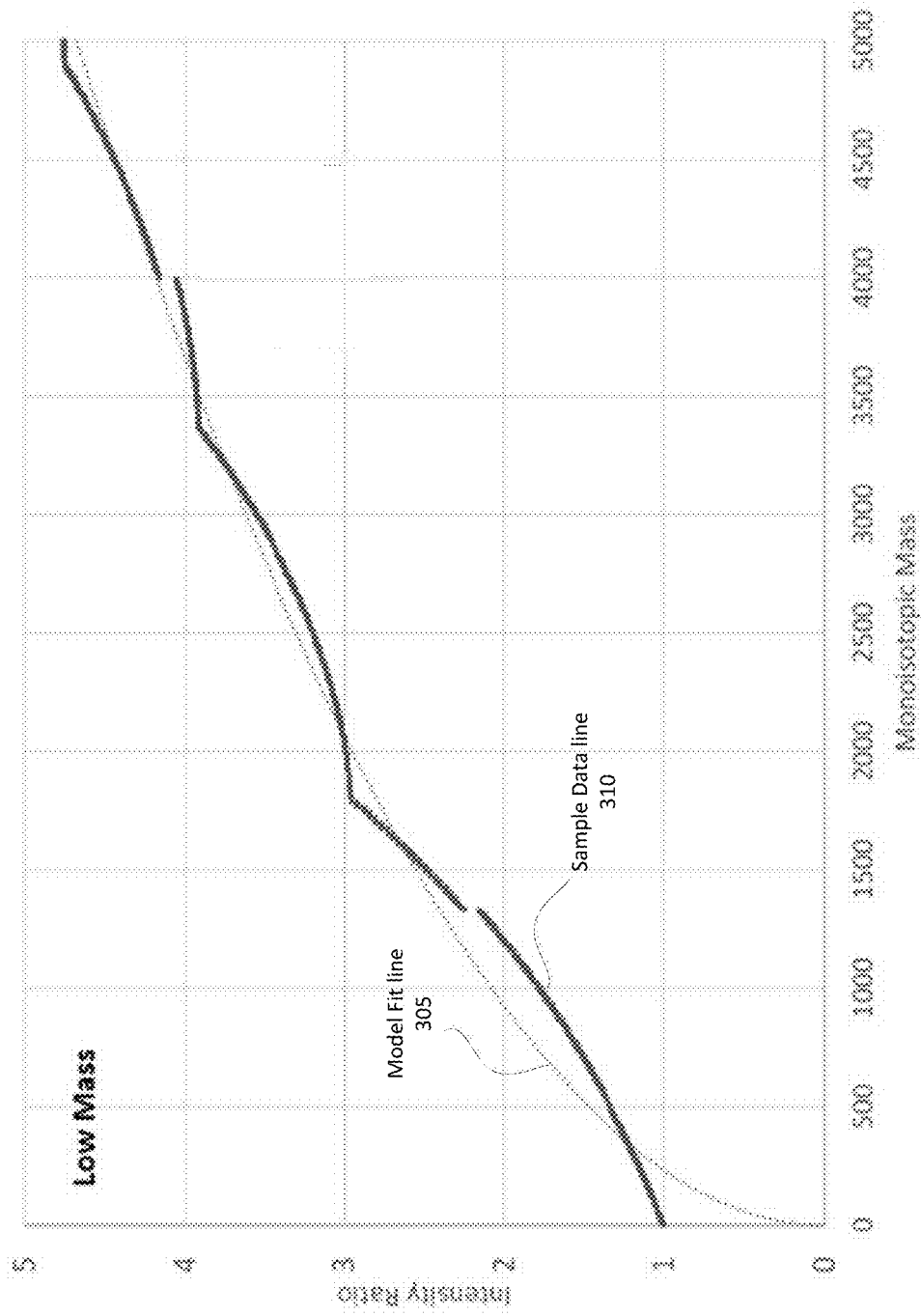

Iteration table 1010

|    |    |    | Offset |   |   |   |   |
|----|----|----|--------|---|---|---|---|
| -4 | -3 | -2 | -1     | 0 | 1 | 2 | 3 |
| -3 | -2 | -1 | 0      | 1 | 2 | 3 | 4 |
| -2 | -1 | 0  | 1      | 2 | 3 | 4 | 5 |

SYSTEM AND METHOD FOR REAL-TIME ISOTOPE IDENTIFICATION

CROSS-REFERENCE TO RELATED APPLICATION

This application claims the benefit of U.S. provisional patent application No. 62/405,452, filed Oct. 7, 2016. The contents of this application are incorporated by reference in their entirety.

FIELD OF THE INVENTION

The invention relates to mass spectral analysis of materials and methods for real-time deconvolution of spectral profiles as well as a quantitative measure of abundance.

BACKGROUND OF THE INVENTION

Mass Spectrometry has been widely used to identify materials present in a sample for a variety of applications. However, real-time analysis of spectral data has proven to be very challenging due to the high level of processing required for accurate spectral deconvolution. Mass spectral analysis of data generated using various techniques that include electrospray ionization (also referred to as "ESI") or laser spray ionization techniques has been particularly challenging because they typically produce ions with the same isotope profiles being detected at multiple charge states due to multiple charging of the analyte molecules. This has generally limited the utility of mass spectral analysis to those applications that do not require having to analyze data in real-time.

The term "real-time" as used herein typically refers to reporting, depicting, or reacting to events at substantially the same rate and sometimes at substantially the same time as they unfold, rather than delaying a report or action. For example, a "substantially same" rate and/or time may include some small difference from the rate and/or time at which the events unfold. In the present example, real-time reporting or action could be also described as "close to", "similar to", or "comparable to" to the rate and/or time at which the events unfold.

Real-time spectral deconvolution, material identification, and reporting are important for a number of reasons. One reason includes the fact that the answers generated are useful to guide decisions that are time sensitive. Some decisions include additional analysis of the subject material that can be made during the same analysis process that produced the original spectral information for the material. For example, the ability to provide real-time decision making power is particularly important in clinical settings where patient outcomes can be significantly improved.

ESI is a technique widely used in Mass Spectrometry applications for producing ion species from macromolecules. In typical applications, analytes of interest are dissolved in a liquid solution and sprayed through an ESI emitter with an electrical potential to produce charged droplets. The droplets carry a charge that, in combination with the effects of solvent evaporation causes production of gas phase ions that include analytes with various charge states. The ions advance to other regions of the mass spectrometer for analysis.

Similarly, with laser spray ionization multiply charged ions can be formed when a sample, fixed to a glass slide and covered with matrix (e.g. 2,5-dihydroxyacetophenone), is struck with a laser pulse from the back of the slide. The resulting ions from the ionization plum are then transferred into the mass spectrometer using an electrical potential. In some cases, laser spray ionization has better efficiency than ESI and ion abundances can be orders of magnitude greater. For example, some embodiments of laser spray ionization provide a better representation of the solution-phase characteristics of certain types of biomolecules or combinations of biomolecules (e.g. protein-DNA interactions).

Recently, advancements in the field of mass spectrometry isotope profile modeling of biological (or polymeric) samples and fitting have made real-time spectral deconvolution more feasible. The first advancement includes the concept of what is sometimes referred to as "Averagine". The Averagine approach produces approximations of the isotope profile models as a function of mass by estimating the elemental composition of the compounds. Examples of the Averagine approach are described in Senko et al., 1995, JASMS, titled "Determination of monoisotopic masses and ion populations for large biomolecules from resolved isotopic distributions", which is hereby incorporated by reference herein in its entirety for all purposes.

A second advancement includes use of isotope look-up tables and charge state determinations that includes an automated fitting process at large scale by fast charge state determination and pre-caching the isotope profiles in look-up tables. One example includes what is sometimes referred to as the "THRASH" algorithm described by Horn et al., 2000, JASMS, titled "Automated reduction and interpretation of high resolution electrospray mass spectra of large molecules", which is hereby incorporated by reference herein in its entirety for all purposes.

A third advancement includes characterizing isotope profiles that were either overlapping by charge (e.g. as described by Zhang et al., 1997, JASMS, titled "A universal algorithm for fast and automated charge state deconvolution of electrospray mass-to-charge ratio spectra, which is hereby incorporated by reference herein in its entirety for all purposes), or intensity (e.g. as described by Renard, 2008, BMC bioinformatics, titled "NITPICK Peak identification for mass spectroscopy data"; or Kronewitter, 2012, Proteomics, titled "The Glycolyzer automated glycan annotation software for high performance mass spectrometry and it application to ovarian cancer glycan biomarker discovery", each of which is hereby incorporated by reference herein in its entirety for all purposes).

Lastly, a fourth advancement included use of exact elemental composition instead of the Averagine approach to develop isotope profile models. The elemental composition approach utilizes knowledge of the material elemental composition a priori to generate one or more isotope profile models for the material (e.g. as described by Kronewitter, 2014, Anal. Chem., titled "GlyQ-IQ glycomics quintavariate-informed quantification with high-performance computing and GlycoGrid 4D visualization", which is hereby incorporated by reference herein in its entirety for all purposes).

In general, the previously described approaches calculate the isotope profiles at run time or perform simple array look-ups of pre-calculated profiles. Unfortunately the previous approaches are too slow and limited in terms of the ability to identify a material from a large pool of candidates while mass spectral information from other materials is being acquired by a mass spectrometer.

Therefore, it is highly desirable to have an analysis approach that substantially increases the speed and performance of processing by a computer in order to provide accurate real-time identification and quantification of compounds for a wide range of applications. For example, increased processing performance completes each task more rapidly thereby freeing up processing resources for other real-time computing tasks that enables rapid and accurate identification and quantification.

SUMMARY

Systems, methods, and products to address these and other needs are described herein with respect to illustrative, non-limiting, implementations. Various alternatives, modifications and equivalents are possible.

An embodiment of a method for real time material identification is described that comprises determining an approximate mass value for an unknown material from spectral information derived from mass spectral analysis of the unknown material; retrieving profile models that correspond to a known material from a data structure using the approximate mass value; fitting a sample profile for the unknown material from the spectral information to the profile models to generate a fit score for each fit, wherein the lowest fit score corresponds to the best fit; calculating a mass value from the best fitting profile model and the sample profile.

In some implementations the method may also include determining the known material corresponding to the best fitting profile model and calculating a measure of abundance of the known material. For instance, the measure of abundance can be calculated by scaling the sample profile by an intensity correction factor. The intensity correction factor relationship can in some instances be calculated using an apex isotope intensity as a divisor of a dividend comprising the sample profile scaled to the apex isotope intensity. Alternatively, the intensity correction factor relationship can calculated using a floating filter area of an isotope profile as a devisor of a dividend comprising the sample profile scaled to the floating filter area of the isotope profile.

Also, an embodiment of a system for calculating a mass value of a material is described that comprises a mass spectrometer adapted to generate spectral information from an unknown material; and a computer having executable code stored thereon, wherein the executable code performs a method comprising: determining an approximate mass value for the unknown material from the spectral information; retrieving a plurality of profile models that correspond to a known material from a data structure using the approximate mass value; fitting a sample profile for the unknown material from the spectral information to the profile models to generate a fit score for each fit, wherein the lowest fit score corresponds to the best fit; and calculating a mass value from the best fitting profile model and the sample profile.

The above embodiments and implementations are not necessarily inclusive or exclusive of each other and may be combined in any manner that is non-conflicting and otherwise possible, whether they are presented in association with a same, or a different, embodiment or implementation. The description of one embodiment or implementation is not intended to be limiting with respect to other embodiments and/or implementations. Also, any one or more function, step, operation, or technique described elsewhere in this specification may, in alternative implementations, be combined with any one or more function, step, operation, or technique described in the summary. Thus, the above embodiment and implementations are illustrative rather than limiting.

BRIEF DESCRIPTION OF THE DRAWINGS

The above and further features will be more clearly appreciated from the following detailed description when taken in conjunction with the accompanying drawings. In the drawings, like reference numerals indicate like structures, elements, or method steps and the leftmost digit of a reference numeral indicates the number of the figure in which the references element first appears (for example, element 120 appears first in FIG. 1). All of these conventions, however, are intended to be typical or illustrative, rather than limiting.

FIG. 3A is a graphical representation of one embodiment of a comparison of results of using a quantitative intensity correction factor to sample material information at relatively low mass;

Like reference numerals refer to corresponding parts throughout the several views of the drawings.

DETAILED DESCRIPTION OF EMBODIMENTS

As will be described in greater detail below, embodiments of the described invention include a substantial improvement in computer processing performance for real-time spectral deconvolution and material identification as well as abundance quantification. More specifically, the invention includes using a hash table data structure to optimize speed of information retrieval, fitting the isotope profile from sample data to a corresponding reference isotope profile model retrieved from the hash table, and summing/averaging multiple charge state sample profiles that correspond to isotopes of a respective material in advance of fitting. In the embodiments described herein, the material may include bacteria, yeast, fungi, proteins, peptides, chemicals, or other materials analyzed via Mass Spectrometry.

Figure 1:
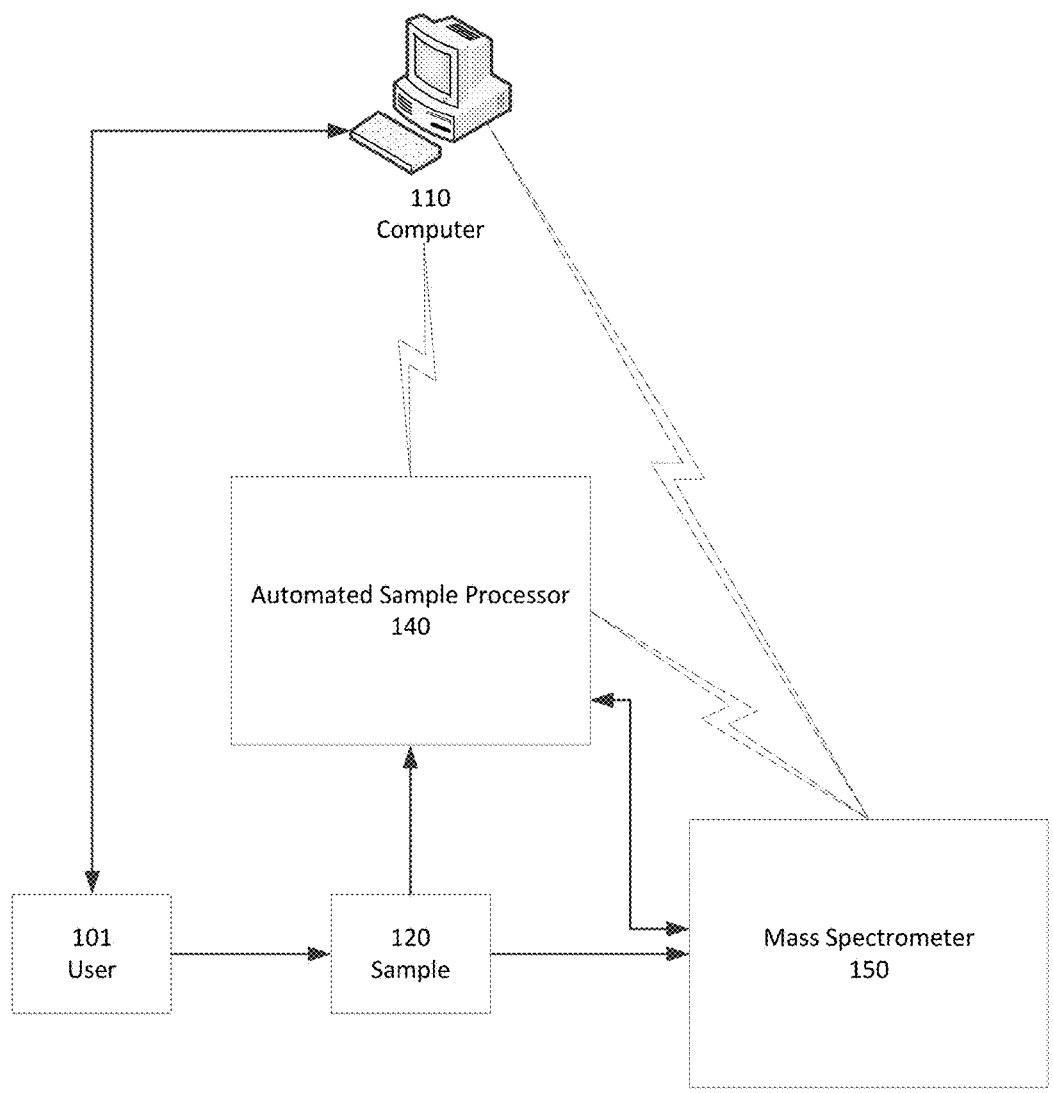
FIG. 1 is a simplified graphical representation of one embodiment of a mass spectrometer instrument and a computer that receives information from the mass spectrometer.

FIG. 1 provides a simplified illustrative example of user 101 capable of interacting with computer 110 and sample 120, as well as network connections between computer 110 and mass spectrometer 150 and between computer 110 and automated sample processor 140. Further, automated sample processor 140 may also be in network communication with mass spectrometer 150. It will be appreciated that the example of FIG. 1 illustrates a direct network connection between elements (e.g. including wired or wireless data transmission represented by lightning bolts), however the exemplary network connection also includes indirect communication via other devices (e.g. switches, routers, controllers, computers, etc.) and therefore should not be considered as limiting.

Also, user 110 may manually prepare sample 120 for analysis by mass spectrometer 150, or sample 120 may be prepared and loaded into mass spectrometer 150 in an automated fashion such as by a robotic platform. For example, automated sample processor 140 receives raw materials and performs processing operations according to one or more protocols. Automated sample processor 140 may then introduce the processed material into mass spectrometer 150 without intervention by user 101. An additional example of an automated platform for processing raw materials for mass spectral analysis is described in U.S. Pat. No. 9,074,236, titled "Apparatus and methods for microbial identification by mass spectrometry", which is hereby incorporated by reference herein in its entirety for all purposes.

Mass spectrometer 150 may include any type of mass spectrometer that transfers charged or uncharged analytes to produce ions for analysis in the form of a mass spectrum. Embodiments of mass spectrometer 150 typically include, but are not limited to, elements, that convert analyte molecules to ions and use electric or magnetic fields to accelerate, decelerate, drift, trap, isolate, and/or fragment, to produce a distinctive mass spectrum. Sample 120 may include any type of sample capable of being analyzed by mass spectrometer 150 such as molecules including biological protein samples. It will be appreciated that the term "molecules" include molecules considered to have a "low mass". Some examples of technologies employed by mass spectrometer 150 instruments include, but are not limited to, time of flight (e.g. TOF), high resolution ion mobility, ion trap, etc. An additional example of a mass spectrometer system useable with some or all embodiments of the presently described invention may include the Thermo Scientific™ Orbitrap Fusion™ mass spectrometer available from Thermo Fisher Scientific of Waltham, Mass. USA.

Some embodiments of mass spectrometer 150 or automated sample processor 140 may employ one or more devices that include but are not limited to liquid chromatograph, capillary electrophoresis, direct infusion, etc. For example, a chromatograph receives sample 120 comprising an analyte mixture and at least partially separates the analyte mixture into individual chemical components, in accordance with well-known chromatographic principles. The resulting at least partially separated chemical components are transferred to mass spectrometer 150 at different respective times for mass analysis. As each chemical component is received by the mass spectrometer, it is ionized by an ionization source of the mass spectrometer. The ionization source may produce a plurality of ions comprising a plurality of ion species (e.g., a plurality of precursor ion species) comprising differing charges or masses from each chemical component. Thus, a plurality of ion species of differing respective mass-to-charge ratios may be produced for each chemical component, each such component eluting from the chromatograph at its own characteristic time. These various ion species are analyzed—generally by spatial or temporal separation—by a mass analyzer of the mass spectrometer and detected via image current, electron multiplier, or other device known in the state-of-the-art. As a result of this process, the ion species may be appropriately identified (e.g. determination of molecular weight) according to their various mass-to-charge (m/z) ratios. Also in some embodiments, mass spectrometer 150 comprises a reaction/collision cell to fragment or cause other reactions of the precursor ions, thereby generating a plurality of product ions comprising a plurality of product ion species.

Also, in some embodiments mass spectrometer system 150 may be in electronic communication with a controller which includes hardware and/or software logic for performing data analysis and control functions. Such controller may be implemented in any suitable form, such as one or a combination of specialized or general purpose processors, field-programmable gate arrays, and application-specific circuitry. In operation, the controller effects desired functions of the mass spectrometer system (e.g., analytical scans, isolation, and dissociation) by adjusting voltages (for instance, RF, DC and AC voltages) applied to the various electrodes of ion optical assemblies and mass analyzers, and also receives and processes signals from the detector(s). The controller may be additionally configured to store and run data-dependent methods in which output actions are selected and executed in real time based on the application of input criteria to the acquired mass spectral data. The data-dependent methods, as well as the other control and data analysis functions, will typically be encoded in software or firmware instructions executed by controller.

Computer 110 may include any type of computer platform such as a workstation, a personal computer, a tablet, a "smart phone", a server, compute cluster (local or remote), or any other present or future computer or cluster of computers. Computers typically include known components such as one or more processors, an operating system, system memory, memory storage devices, input-output controllers, input-output devices, and display devices. It will also be appreciated that more than one implementation of computer 110 may be used to carry out various operations in different embodiments, and thus the representation of computer 110 in FIG. 1 should not be considered as limiting.

In some embodiments, computer 110 may employ a computer program product comprising a computer usable medium having control logic (computer software program, including program code) stored therein. The control logic, when executed by a processor, causes the processor to perform functions described herein. In other embodiments, some functions are implemented primarily in hardware using, for example, a hardware state machine. Implementation of the hardware state machine so as to perform the functions described herein will be apparent to those skilled in the relevant arts. Also in the same or other embodiments, computer 110 may employ an internet client that may include specialized software applications enabled to access remote information via a network. A network may include one or more of the many various types of networks well known to those of ordinary skill in the art. For example, a network may include a local or wide area network that employs what is commonly referred to as a TCP/IP protocol suite to communicate. A network may include a network comprising a worldwide system of interconnected computer networks that is commonly referred to as the internet, or could also include various intranet architectures. Those of ordinary skill in the related arts will also appreciate that some users in networked environments may prefer to employ what are generally referred to as "firewalls" (also sometimes referred to as Packet Filters, or Border Protection Devices) to control information traffic to and from hardware and/or software systems. For example, firewalls may comprise hardware or software elements or some combination thereof and are typically designed to enforce security policies put in place by users, such as for instance network administrators, etc.

Figure 2:
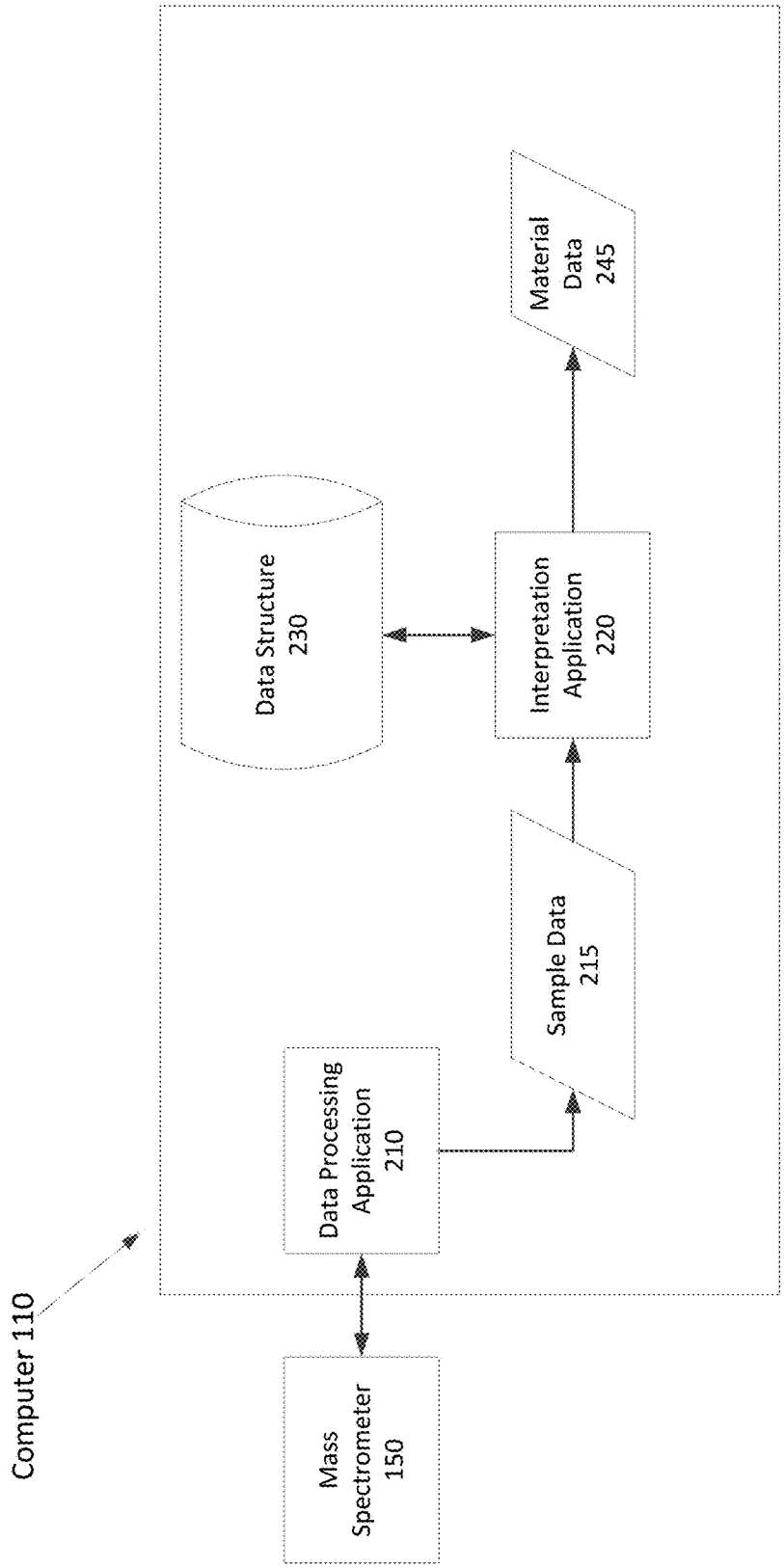
FIG. 2 is a functional block diagram of one embodiment of the mass spectrometer and computer of FIG. 1 with an interpretation application in communication with a data structure.

Also, as described above computer 110 may store and execute one or more software programs configured to perform data analysis functions. FIG. 2 provides an illustrative example of an embodiment of computer 110 comprising data processing application 210 that receives raw mass spectral information from mass spectrometer 150 and performs one or more processes on the raw information (e.g. one or more "mass spectra") to produce sample data 215 useable for further interpretation. For example, one embodiment of data processing application 210 processes the spectral information associated with a material and outputs information such as a known material identified by the analysis of a sample of unknown materials, a value of the mass of the material analyzed (e.g. a monoisotopic mass, or an average mass value), and/or modified spectral profiles from the material (e.g. includes "centroids" that reduces the amount of data needed to characterize the profile). The term "monoisotopic mass" as used herein should be interpreted according to the understanding of those of ordinary skill in the related art and generally refers to the sum of the masses of the atoms in a molecule using the unbound, ground-state, rest mass of the most abundant isotope for each element. Also, the term "centroid" as used herein should be interpreted according to the understanding of those of ordinary skill in the related art and generally refers to a measure used to characterize a spectrum where the centroid indicates where the center of mass is located based on the modeled apex of the profile peak. Additional examples of software program for data processing are described in U.S. Patent Application Publication No. US 2016-0268112 A1, titled "Methods for Data-Dependent Mass Spectrometry of Mixed Biomolecular Analytes", filed Mar. 11, 2016, which is hereby incorporated by reference herein in its entirety for all purposes.

As described above, embodiments of the invention include systems and methods for a real-time spectral deconvolution, material identification, as well as abundance quantification. More specifically, the invention includes employing a hash table data structure, illustrated as data structure 230 in FIG. 2, to store and enable rapid identification of appropriate reference models and other related data. Those of ordinary skill in the art appreciate that other types of data structure could also be employed with the presently described embodiments, and thus the description of a hash table data structure should not be considered as limiting. For example, data structures that enable fast data retrieval may include trees, hashes, graphs, non-simple lists, or other data structures known in the art for efficient data retrieval.

Importantly, interpretation application 220 aligns and fits the material information in sample data 215 to the reference models retrieved from data structure 230, rather than fitting the reference models to the material information in the sample data which has been the historical approach. The embodiments of the presently described invention provide significant improvements in the speed of fitting profile models and sample profiles together over prior art approaches. For example, each profile retrieval may require about 1.36 μs to execute and the full process of fitting may require about 13 μs to execute using computer 110 with the appropriate processing power typical for embodiments of attendant computing devices for mass spectrometry.

It will also be appreciated that although FIG. 2 illustrates data processing application 210 and interpretation application 220 as separate elements, the functions of both application 210 and 220 as described herein may be performed by a single application. Further some functions described as performed by application 210 may be performed by application 220 and vice versa. Therefore the example illustrated in FIG. 2 should not be considered as limiting.

Some embodiments of the invention include generating a cache of pre-computed isotope profile model information in a hash table data structure prior to testing sample materials with mass spectrometer 150 so that only a minimal number of calculations on sample data 215 are required at run time. It will be appreciated by those of ordinary skill in the related art that the processing time required to produce material data 245 decreases by minimizing the number of calculations performed during the process. In some embodiments the isotope profile models may include any experimentally derived or theoretical models. In one possible example, the isotope profile models may be calculated using the Averagine method described above. Those of ordinary skill understand that the Averagine method may use any average unit, or units, appropriate for the sample. Alternatively, the isotope profile models may be calculated using the elemental composition approach, as also described above, if the elemental information for a material is known a priori. Also, some combination of the Averagine and elemental composition approaches may be employed. Further, some combination of two or more isotope profile models for the same material can be used if the sample contains both chemically labeled and non-labeled molecules.

The use of a hash table data structure provides an extremely fast data retrieval mechanism where the time required to return information scales with an average of the search times that are constant expected time t(1). For example, the theoretically worst case scenario scales with t(n) for search times, where "n" for material identification purposes can be on the order of a hundred thousand or more. Importantly, due to the use of a "balanced" hashing approach, interpretation application 220 can operate in an t(1) scenario and the t(n) scenario is avoided. As those of ordinary skill in the art appreciate, balanced hashing, sometime also referred to as "consistent hashing" generally refers to consistently mapping of objects in the hash table as new objects are added. Therefore the hash key will consistently point to the correct object in the hash table. For example, the balanced hashing approach translates to extremely fast key searches taking around 1-2 μs (or faster) per isotope profile to complete using computer 110 with the appropriate processing power typical for embodiments of attendant computing devices for mass spectrometry. In contrast, standard look up tables can take more than twice as long. In the described example, interpretation application 220 can analyze data in ~10 µs (or faster) per profile (post charge deconvolution).

In addition to caching the isotope profile models, embodiments of the invention may also include a cache of "iteration tables" in the hash table data structure. The term "iteration table" as used herein generally refers to information stored in a table format pre-computed from known isotope profile models of the material. The iteration tables enable fast alignment of the sample profiles to the isotope profile models by providing the ability to discretely shift the sample profile by some degree specified in the iteration table known to be associated with an isotope of the material. For example, the iteration table comprises columns with "offset" values that correspond to a degree and direction of shift (e.g. +/− in Da) from the peak centroid. For every iteration, a shift from the iteration table is applied and the fit score calculated. In the present example, every row corresponds to the offset values pre-calculated from known isotope profiles.

Further, all mass (e.g. monoisotopic mass, or average mass) and score parameters for the materials of interest are also cached in the data structure. In some embodiments, one or more quantitative intensity correction factors are also cached or can be calculated in real-time to provide an improved result, particularly for materials having relatively high masses or those detected near the noise level. Also, in the described embodiments this can enable calculation of an accurate measure of material abundance by integrating (e.g. summation) the theoretical isotope profile models and dividing the integrated value by the measured intensity at the apex of a sample isotope profile.

For example a quantitative intensity correction factor can be calculated by the following equation:

$$\text{Quantitative Intensity Correction Factor} = X \text{ Mass}^Y$$

X and Y are fit coefficients appropriate for the fitting the intensity correction factor to the selected isotope profile set or sets used. For example, the human Averagine estimation may use X=0.064247 and Y=0.503492, but other coefficients may be substituted as applicable.

Figure 3B:
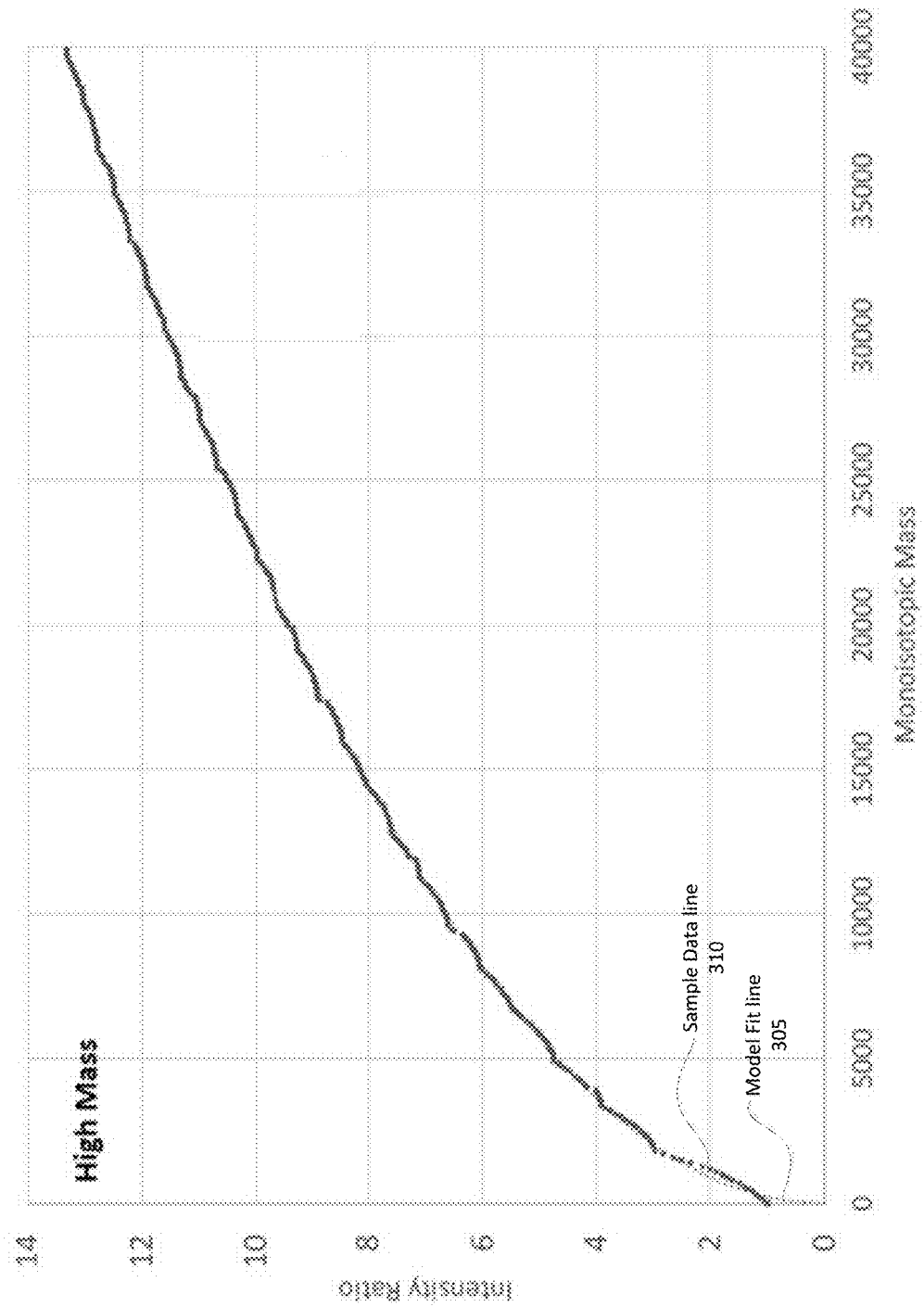
FIG. 3B is a graphical representation of one embodiment of a comparison of results of using the quantitative intensity correction factor to sample material information at relatively high mass.

Continuing with the present example, it will be appreciated that other similar coefficients or equations for calculating the quantitative intensity correction factor can be used and thus the equation presented herein should not be considered as limiting. FIGS. 3A and 3B provide illustrative examples comparing the results of using the quantitative intensity correction factor to the material information in sample data 215. More specifically, FIG. 3A illustrates a plot at low mass where model fit line 305 (e.g. calculated using the quantitative intensity correction factor) deviates from the monoisotopic mass values in sample data 215. Importantly, at relatively low mass values (e.g. ~1500 Da and lower) sample data line 310 provides a better measure of the intensity ratio than the model fit line 305 and should be cached and retrieved from the data structure since the intensity ratio should not go below 1. In contrast, FIG. 3B illustrates a plot at high mass where model fit line 305 provides a good representation for the monoisotopic mass values in sample data 215. Thus for relatively high mass values it will be appreciated that either the values calculated using the quantitative intensity correction factor or calculated model can be used to provide good results.

Appropriate caching of information may decrease the run time required by around 98% as compared to binary searches with look up tables, and provides for faster processing time than more complicated algorithms that calculate one or more isotope profile models for each profile during run time.

Figure 4:
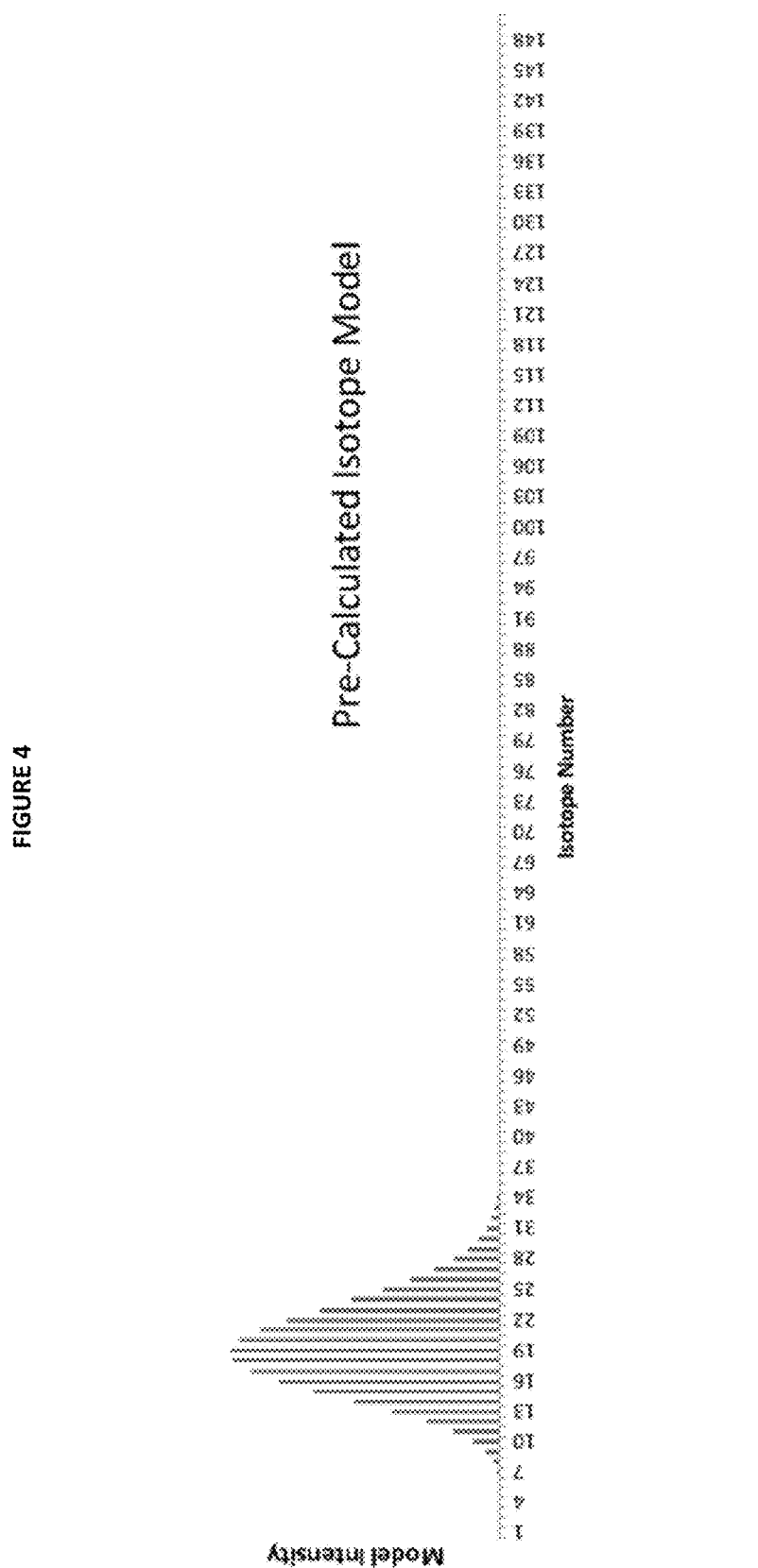
FIG. 4 is a simplified graphical representation of one embodiment of a pre-calculated isotope profile model.

As described above, calculating isotope profile models is a computationally expensive process where the computational cost increases with increases in mass of the material. Thus, calculating the profile models in advance and storing them for later use drastically decreases the real-time processing requirements for molecular mass determination. Typical isotope profile models are probability distributions as illustrated in the example of FIG. 4 that shows a pre-calculated isotope profile model for a material having a peak at mass 19 kDa. The isotope number (e.g. scale on X axis) in the example of FIG. 4 includes 148 isotopes due to the fact that about 150 isotopes provide a suitable range for embodiments of the invention. However, larger or smaller ranges of isotope number may be suitable for corresponding larger or smaller mass ranges as the isotope number typically correlates with the monoisotopic mass of a compound. Also, in the described embodiments the profile model may be processed and represented as centroid values that are displayed as discrete mass to charge ratio (e.g. sometimes represented as "m/z") with zero line widths. The advantage of centroid data is the file size is significantly smaller as there is less information needed to describe the profile model.

Determining the quantitative intensity correction factor can also be a computationally expensive process. The intensity correction factor is the relationship between the measured intensity at the apex isotope of a sample isotope profile to the full area of the modeled reference isotope profile which includes all isotope peaks in the model. As described above, a measure of material abundance can be calculated by scaling the intensity of the apex isotope of a sample isotope profile by the intensity correction factor. Alternatively the relationship between the floating filter areas and model reference isotope profile can be used in place of the apex based relationship. The area defined by the "floating filter" is sometimes preferred because it helps reduce uncertainty when the measured intensity at the apex of an isotope profile varies due to poor ion statics or noise. Either profile or centroid (e.g. peak apex only) peak data can be used in the model building process and as sample data.

Figure 5:
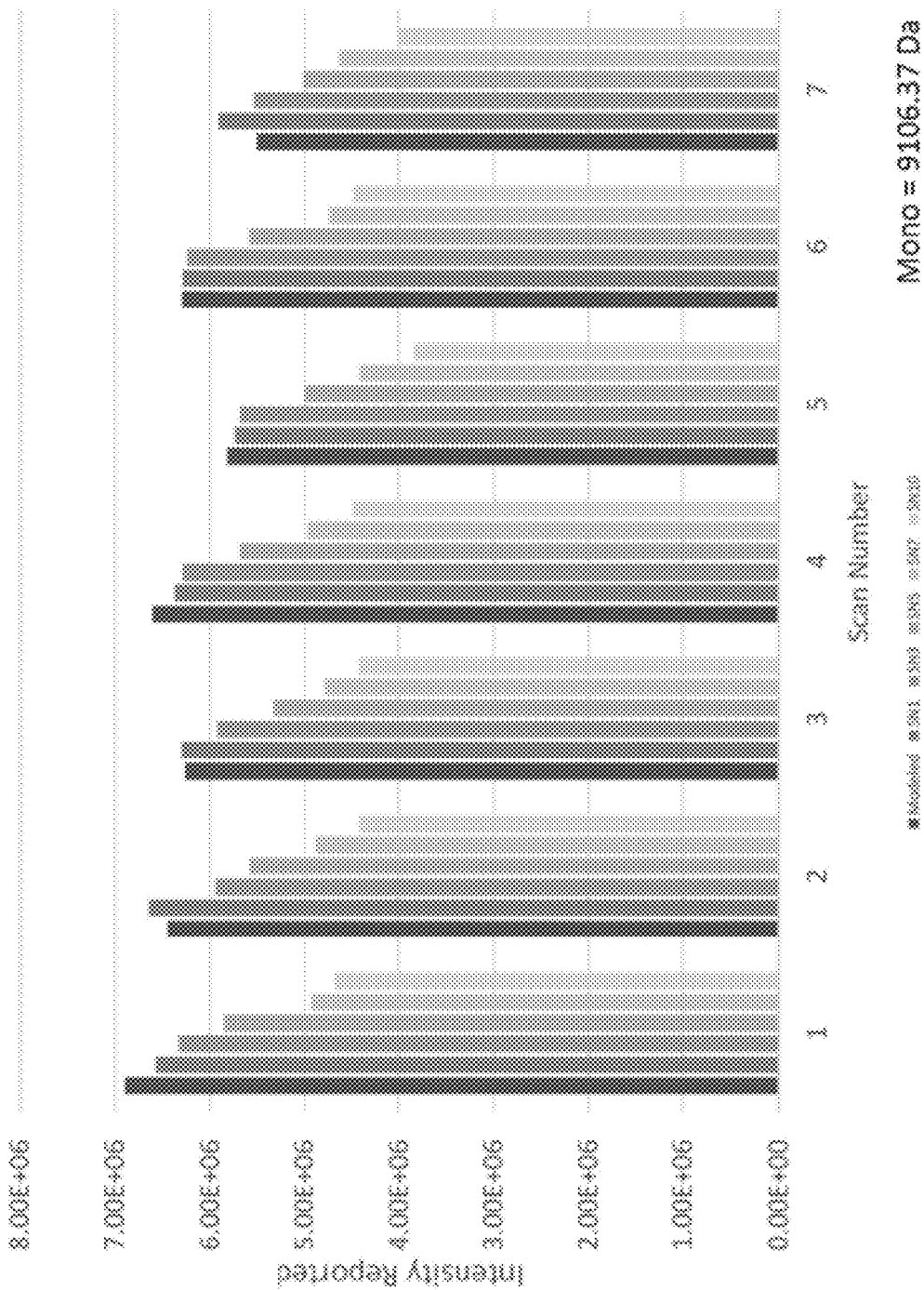
FIG. 5 is a simplified graphical representation of one embodiment of the modeled versus measured reported summed intensity of a sample isotope profile for a number of scans used to calculate a measure of abundance for a material.

FIG. 5 provides an illustrative representation of the modeled versus measured intensity at the apex of an isotope for a number of scans used to calculate a measure of abundance for a material having a monoisotopic mass value of 9016.37 Da. For example, the reported summed intensity corresponds to the summation of the intensities for each of the isotopes detected. The "Modeled" series corresponds to the modeled intensity described herein for a monoisotopic mass of 9106.37 Da and all isotopes in the model are summed. The "SN1", "SN3", "SN5", "SN10" series represent the intensity where isotopes detected below the signal to noise threshold (e.g. peaks less than signal/noise=5 for SN5) are not included in the summed intensity calculation generally yielding lower than expected values. In the described example, interpretation application 220 may calculate a measure of abundance of a known material that corresponds to a best fitting reference profile model (e.g. as will be described in greater detail below) by integrating the best fitting isotope profile model and dividing the integrated value by a measured intensity at an apex of the sample profile.

Figure 6:
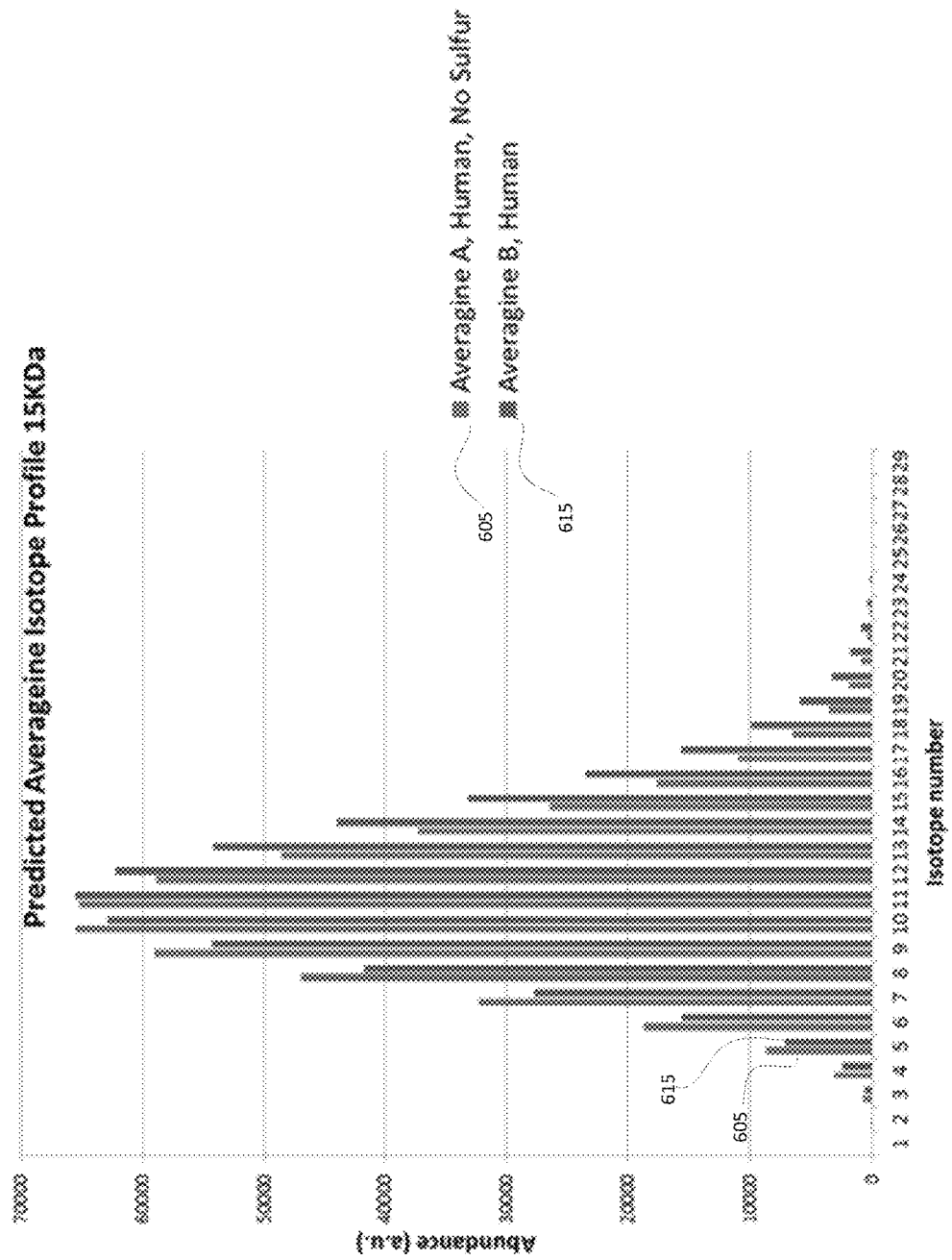
FIG. 6 is a simplified graphical representation of one embodiment of the differences between pre-calculated isotope profile models based on composition difference of comparable compounds.

Some embodiments of the invention may create multiple hash table data structures that each correspond to the source of a substantially similar and comparable material which may have unique characteristics. Alternatively, separate instances for the substantially similar and comparable materials may be created in the same hash table data structure, each instance corresponding to one of the unique characteristics. If the instances are sufficiently distinct it is possible to separately identify the source of the substantially similar material. For instance, some materials may have composition characteristics of a source that affect the calculated distributions of the profile models for a material such as the presence/absence of sulfur or carbohydrates. FIG. 6 provides an illustrative example of isotope profile models of comparable compounds (e.g. proteins) comprising composition differences. More specifically, the example of FIG. 6 demonstrates a shift in profile 605 distribution attributable to the presence of sulfur in protein material in Humans whereas sulfur is not seen in the substantially similar in profile 615 in protein material from bacteria.

Some embodiments of the presently described invention may also utilize what may be referred to as an "area filter" (also sometimes referred to as a "floating filter") to isolate the most accurate areas of the full isotope models. The floating filter version of the isotope profile models are then stored in the hash table data structure. An illustrative example of floating filtered isotope profile models is provided in FIG. 7. This shows that isolation of the profile model to the area centered on the most abundant peak of the profile eliminates some percentage of the total profile area in the tail areas of the profile curve.

Those of ordinary skill in the related art appreciate that the full isotope profile models require a significant amount of data storage capacity and therefore use of the floating filter decreases the amount of data needed to store in the hash table data structure. In addition the data representing the isotope profile models produced by applying the floating filters is optimal for fitting in the embodiments described herein. For example, the information content of the profile models produced from the floating filters is increased over the unfiltered profiles because only the isotope peaks with the highest signal to noise ratio are used in the fitting of sample data 215 to the profile models.

Figure 7:
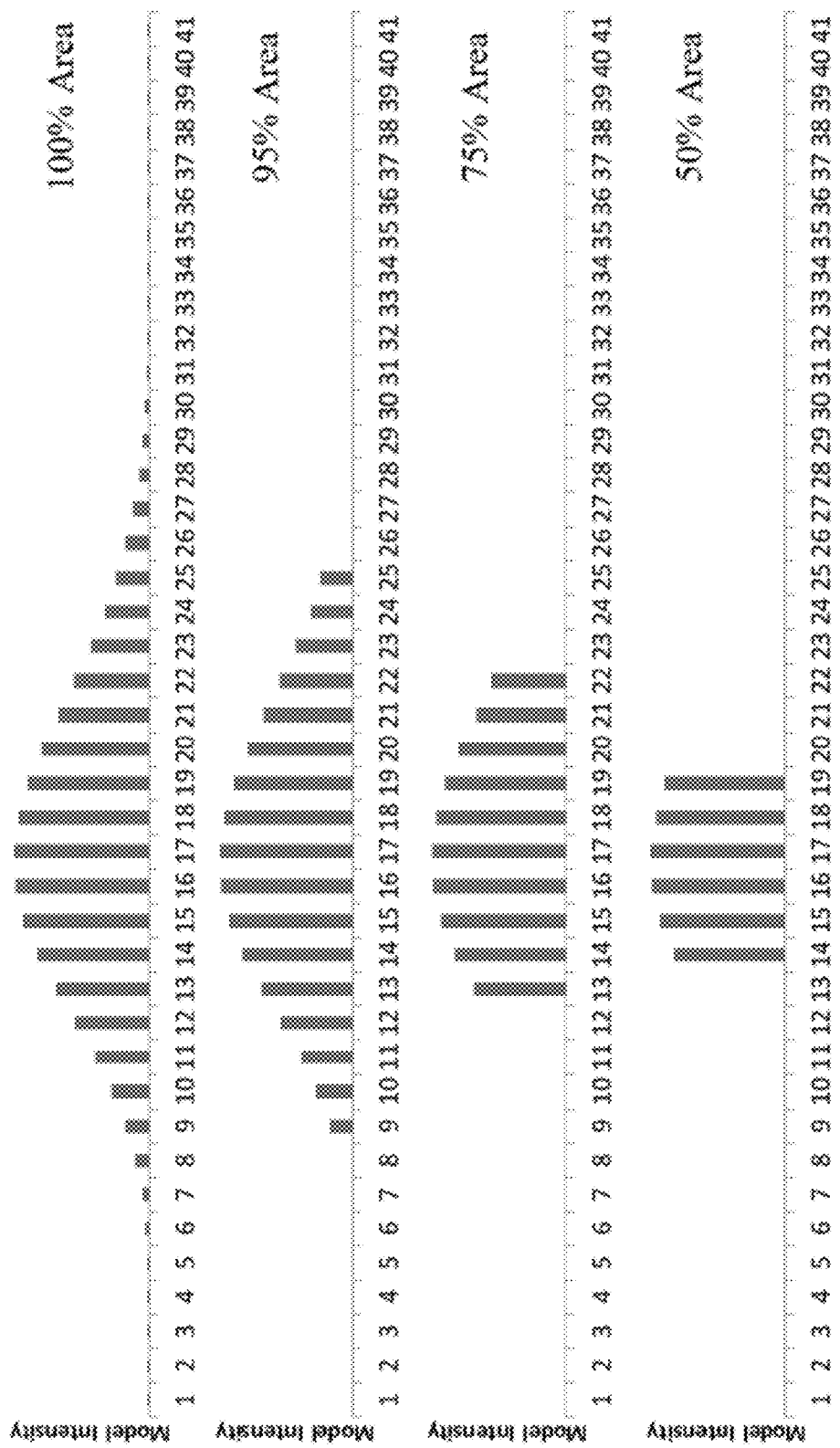
FIG. 7 is a simplified graphical representation of one embodiment of a pre-calculated isotope profile model with different floating area filters applied.

In some embodiments, a library of full isotope profile models for materials of interest is obtained and a floating filter to each of the isotope profile models is applied. The degree of coverage of the floating filter (e.g. by percentage as illustrated in FIG. 7) may be user defined, preset to a predefined value, defined based on one or more criteria associated with computational performance of fitting the area filtered profiles to sample data 215, or other metric. For example, the area percentage of the isotope profile models used for the floating filter may be defined by confidence levels, based on the number of analytes in the sample data or mass range of interest. In the present example, an isotope profile with a narrow width and high intensity may use a higher percentage of total profile area than an isotope profile with a wide width and low peak intensity (e.g. with long tails).

In some embodiments a clustering approach can be employed to improve results of the deconvolution strategies described herein. As those of ordinary skill in the related art appreciate, isotopes of a material should differ from each other by about 1 Da increments in mass due to the fact that the mass of a neutron is about 1 Da (e.g. isotopes of a material have different numbers of neutrons). Therefore, some embodiments the floating filter may also include what is referred to as a "comb filter" that include "teeth" parameters that differ from each other by 1 Da increments on a scale or axis. For example, the comb filter can be used to cluster isotope profiles belonging to the same material across scans or between datasets. In some cases, poor data quality (e.g. ion statistics) can lead to undesirable under sampling of the sample isotopic profiles that can subsequently lead to model fitting errors because there is not enough isotopic profile information of sufficient quality. In the present example, the model fitting errors propagate to discrete errors (±n Da) when determining the monoisotopic mass. Thus, during clustering two or more profiles of varying data quality, the error will be consistent for all isotopes of the same sample material (e.g. material with a particular mass) and thus with the teeth parameters of the comb filter.

Figure 8:
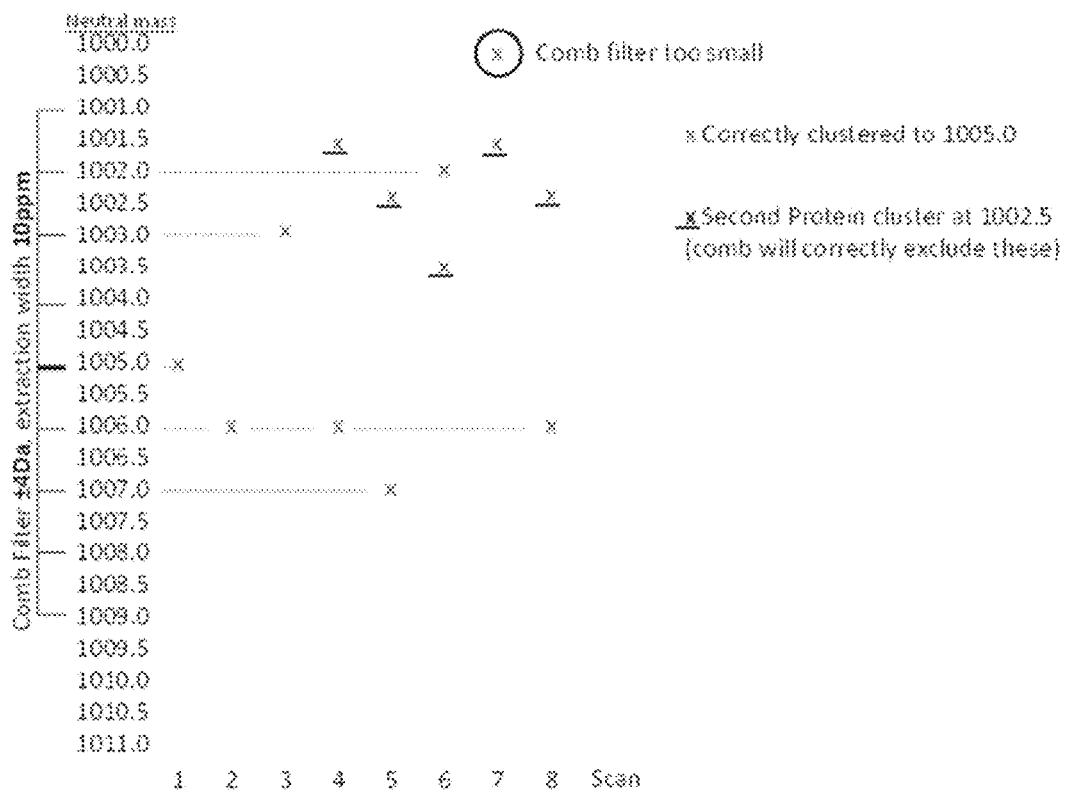
FIG. 8 is a simplified graphical representation of one embodiment of the floating area filter of FIG. 7 comprising an isotope comb filter.

FIG. 8 provides an illustrative example of the comb filter concept that illustrates the case where the profiles of two proteins overlap. For instance the floating filter automatically pre-sets the size of the window of the comb filter due to the increased certainty that the isotope profile model accurately represents isotopes of a single material. In the example of FIG. 8, data points that do not correspond to the teeth spacing for a first material belong to a second material allowing for high resolution differentiation of materials with similar but distinctive masses. It will also be appreciated that additional statistical analyses may be used to further refine and/or verify the clustering.

The computed floating filtered profile models for each known isotope of the material of interest are then cached in the hash table of data structure 230. In some or all of the described embodiments, a value of the mass of the material of interest (e.g. an integer value) may be used as the key to the information stored in the hash table. Also, in addition to caching floating filtered profile models for each isotope, the respective iteration tables for the material of interest are cached based on the same key. Storing minimal, information-rich profile models and non-redundant iteration tables help limit the memory footprint of the hash table data structure and decrease run time when retrieving information from the hash table data structure.

In some embodiments, the sample isotope profiles in sample data 215 may include what are referred to as "unresolved" profile models. Those of ordinary skill in the related art appreciate that the term "unresolved" profile or mass spectrum as used herein includes a profile that contains partially or non-resolved isotope peaks. It is also appreciated that unresolved sample isotope profiles present a challenge for determining the monoisotopic mass value. Resolution, is typically defined as m/Δm or mass/peak width (e.g. at what is referred to as "Full Width at Half Maximum" (FWHM)). In some or all of the described embodiments the FWHM for resolution may be calculated using mathematical functions known to those of ordinary skill in the art. For example, FWHM is a parameter commonly used to describe the width of a peak on a spectrum and the formula used to calculate FWHM depends, at least in part, on the shape of the peak or curve (e.g. Gaussian, Lorentzian, Welch, Connes, Sync, etc.). In the present example a variety of FWHM formulas may be chosen for the calculation and it is not critical which algorithm is used as long as the same algorithm is consistently used for the measurements.

One embodiment of the described invention uses the populated hash tables (fully defined reference isotope distribution models) as described above as a resource for models for fitting to unresolved sample isotope profiles for accurate monoisotopic mass determination. It will be appreciated that the floating filter may be used with the reference isotope profile models as described above to fit to the unresolved sample isotope profile. Also, similar to the use of the isotope iteration tables described above interpretation application 220 can iteratively fit the unresolved sample isotope profiles to the full reference isotope profile models. Since the individual isotopes in the unresolved sample isotope profile models are not fully resolved (e.g. the degree of resolution is too low to provide individual isotope centroids in the profile), the fitting procedure is not restricted to integer values akin to the comb filter. For example, application 220 calculates the optimal fit of the unresolved sample profile to the full reference isotope profile model using the "geometric centroid" of the sample profile. The term "geometric centroid" as used herein generally refers to the center of mass of the sample isotope profile or the centroid (in the mass dimension) at the peak apex (e.g. modeled or approximated from the sample data). Knowing the mass value associated with the geometric centroid of the sample isotope profile, the mass value associated with the geometric centroid of the reference isotope profile model, and the known difference in mass between the geometric centroid of the reference isotope profile model and the monoisotopic mass, the monoisotopic mass can be calculated. In the described example, errors can occur when the sample isotope profile data is not well represented by the reference isotope profile models cached in the hash table or if the data quality is poor (e.g. poor ion statistics).

Figure 9:
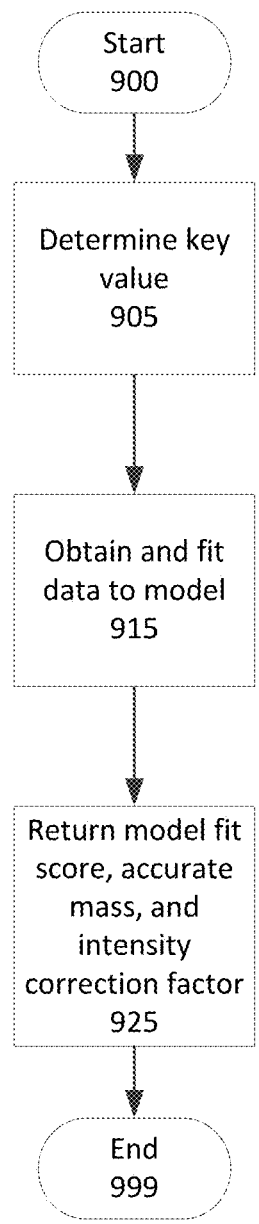
FIG. 9 is a functional block diagram of one embodiment of a process for fitting a sample profile data for an unknown material to a profile model and determining an accurate mass for the material.

FIG. 9 provides an example of a workflow for identifying a material that includes step 905 to determine which hash key corresponds with the corresponding material data so the proper model is returned. In the embodiments described herein, data processing application 210 is able to calculate an approximate monoisotopic mass or an average mass value for each material from the data received from mass spectrometer 150, the approximate monoisotopic mass values or average mass values are output as sample data 215. The approximate monoisotopic mass value or the average mass value can then be used to extract a reference model likely to correspond to the material. For example, the appropriate key to the hash table data structure may be generated by truncating, rounding, ceiling, or flooring the decimal fraction from the approximate monoisotopic mass value leaving the integer value of the approximate monoisotopic mass as the key value. The process of truncation is computationally several times faster than rounding or flooring values and orders of magnitude faster than interpolation methods. The key can be used to return the profile models, the iteration table, and other information that may include meta-data about the model.

As illustrated in step 915, interpretation application 220 employs the key value to retrieve the profile models and iteration tables from the hash table data structure. Interpretation application 220 then aligns the information in sample data 215 to the reference isotope profile models and evaluates the quality of the fit. In some embodiments what is referred to as a "goodness of fit" statistical approach may be employed to determine whether the distribution of data points in the sample isotope profile from sample data 215 is statistically the same as the distribution of data points of the reference isotope profile model from the hash table. It will be appreciated that goodness of fit approaches generally produce a measure of the difference, or fit error, between observed sample values and the expected values for the profile in question that is may be referred to as a "fit score". As described above, the approach of the described embodiments is to fit the sample isotope profile from sample data 215 to the reference isotope profile models (e.g. reference models) and thus the method determines a fit score representing how well the sample isotope profile fits to the reference isotope profile model, where the lowest fit score, having the least error, corresponds to the best fit.

Also as described above, the iteration tables retrieved with the model include arrays of integers that include "offset" values between the most abundant point of the reference isotope profile model data points and the sample isotope profile data points. In other words, testing the goodness of fit with the reference isotope profile model offset in a direction and the degree of the value. For example, the center of the sample isotope profile represented by the most abundant centroid may be positionally translated by the value in the table for the iteration and the goodness of fit with the reference isotope profile model tested to determine the lowest value for goodness of fit.

Figure 10:
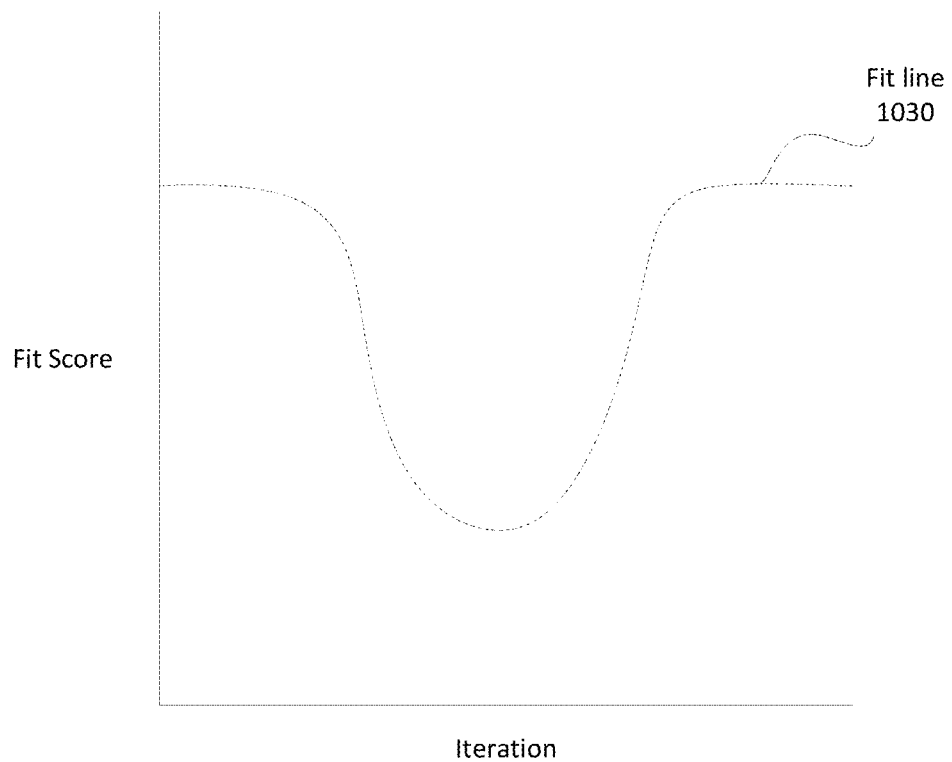
FIG. 10 is a simplified graphical representation of one embodiment of an iteration table and a graph illustrating a relationship of a fit score obtained when applying shifts defined in the iteration table.

FIG. 10 provides an illustrative example of an iteration table and a graph depicting the relationship of a fit score obtained when applying shifts defined in the iteration table. In some embodiments, the iteration table includes integer values that represent index shifts between the isotopes of the model and the isotopes of the sample. As illustrated in FIG. 10, iteration table 1010 contains information used to efficiently offset the sample isotope profile data with respect to the reference isotope profile model by incremental values for finding the optimal fit between the data and the model. The information in iteration table 1010 includes a row for each isotope profile for a material of interest. The offset values in the iteration tables can be applied to shift the sample profile in sample data 215 by the degree of offset value to obtain a fit score for the profile model associated with the approximate mass of the unknown material identified in sample data 215. At each iteration the fit score is calculated where the lowest fit score corresponds to the best fit between sample isotope profile and the reference isotope profile model at the offset for that iteration defined in the iteration table (e.g. an illustrative example is provided as fit line 1030 in FIG. 10). Since many reference isotope profile models have the same number of isotopes in the model, duplicate iteration table entries in the hash table can be removed to improve retrieval speed and decrease memory usage. In the described example, the "0" value represents the position of the center of the profile for the iteration.

In some or all of the described embodiments, interpretation application 220 iterates through each row of the iteration table to apply the offset values to translate the positions of the centroid peaks in the sample isotope profile by the value in the table (e.g. in Daltons) and calculate the goodness of fit to the reference isotope profile model. The offset values in the rows can either be in order (e.g. sequential order of translation such as 1, 2, 3, 4, etc.), or staggered order (e.g. 3, 1, 4, 2, etc.) so long as all relevant alignments are tested. The iteration table is determined by the integer hash key, respective floating filter range and the difference between the most abundant sample isotope centroid in the data and the most abundant isotope in the reference isotope profile model. A fixed number of start points are used to sufficiently account for noisy sample profiles where the most abundant isotope centroid is not the central isotope centroid.

In some embodiments, sample isotope profiles to be fit can include a sample isotope profile corresponding to a single charge state, or alternatively the sample isotope profile may include an average sample isotope profile produced from sample profiles from multiple charge states. Averaging the sample profile data from multiple charge states reduces noise and improves the shape of the sample profile data used for the fitting process. To fit the model, the data is incremented across each line in the iteration table to generate a candidate alignment.

As illustrated in step 925, interpretation application 220 sorts the fit scores and determines the lowest score that corresponds to the best fit. The corresponding row in the iteration table indicates the best alignment between the sample profile and the profile model allowing for rapid identification of the optimal profile model. For example, the theoretical monoisotopic mass value may be approximately 10 Da less than the mass value of the most abundant peak in the profile model. However, it will be appreciated that the degree of difference between the theoretical monoisotopic mass value and the mass value of the most abundant peak in the profile model may vary depending on various factors. In some embodiments, application 220 calculates the monoisotopic mass value for each one of the isotope points in the sample profile, and determines an average monoisotopic mass using the multiple data points, further increasing its accuracy. Also, interpretation application 220 may return an intensity correction factor used to determine the measure of abundance for the material identified by the reference isotope profile model fit to the data. Further, at step 925 interpretation application may also determine the known material that corresponds to the best fitting profile model and return the information to user 101.

Figure 11:
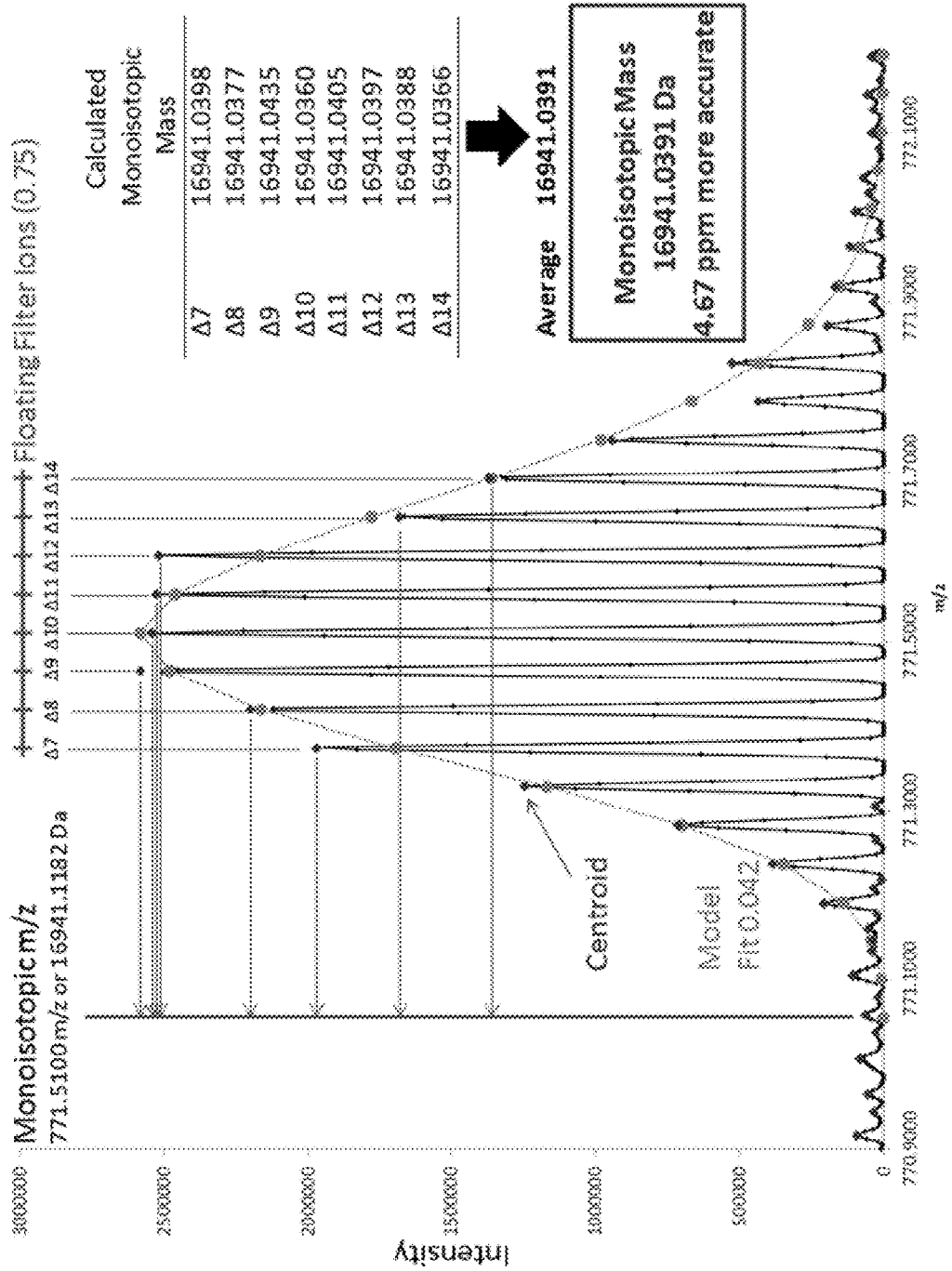
FIG. 11 is a simplified graphical representation of one embodiment of a mass calculation using the best fitting sample isotope profile to a reference isotope profile model.

FIG. 11 provides an illustrative example of a mass calculation using the best fitting sample isotope profile to a reference isotope profile model. The sample isotope profile includes a distribution of isotope peaks (e.g. depicted as a "saw tooth" profile of lines and dots) derived from a protein with a monoisotopic mass value of 16941.0391. Each peak in the sample isotope profile distribution comprises a centroid (e.g. each depicted as a small diamond). The theoretical isotope profile illustrated in the example of FIG. 11 was iteratively fit to the sample isotope profile distribution until the optimal fit was determined having a fit score of 0.042 (e.g. depicted as the dashed line). The top of FIG. 11 also illustrates a series of delta mass values depicting the relationship of each individual isotope peak to the monoisotopic mass value (e.g. the isotope peak at 49 is approximately the monoisotopic mass value+9 mass units). The term "mass unit" as used herein typically refers to a value that is the average C12-C13 mass difference which is similar in mass to the mass of a neutron. Further, the position of the monoisotopic mass value is represented in FIG. 11 by the thick vertical line at about m/z=771 (charge state+22) which corresponds to 16941.0391 Da that is approximately 10 Da away from the peak centroid of the full sample profile (e.g. high resolution).

Continuing with the example illustrated in FIG. 11, the table in the upper right section illustrates the calculated monoisotopic mass value from each isotope as well as an average value of the calculated monoisotopic mass values that provides a more accurate value of monoisotopic mass value. It will be appreciated that use of the average value should not be considered as limiting and that other data consolidation methods could also be used, including but not limited to weighted average, mean, mode, medial mass, or mass to charge values. In the presently described example only the most abundant isotope centroids were selected for the average calculation using the floating filter (e.g. using the floating filter set to select 75% of centriods which are most abundant). The accuracy and speed of the calculation is improved by elimination of the error prone low abundance centroids from the sample isotope profile.

Figure 12:
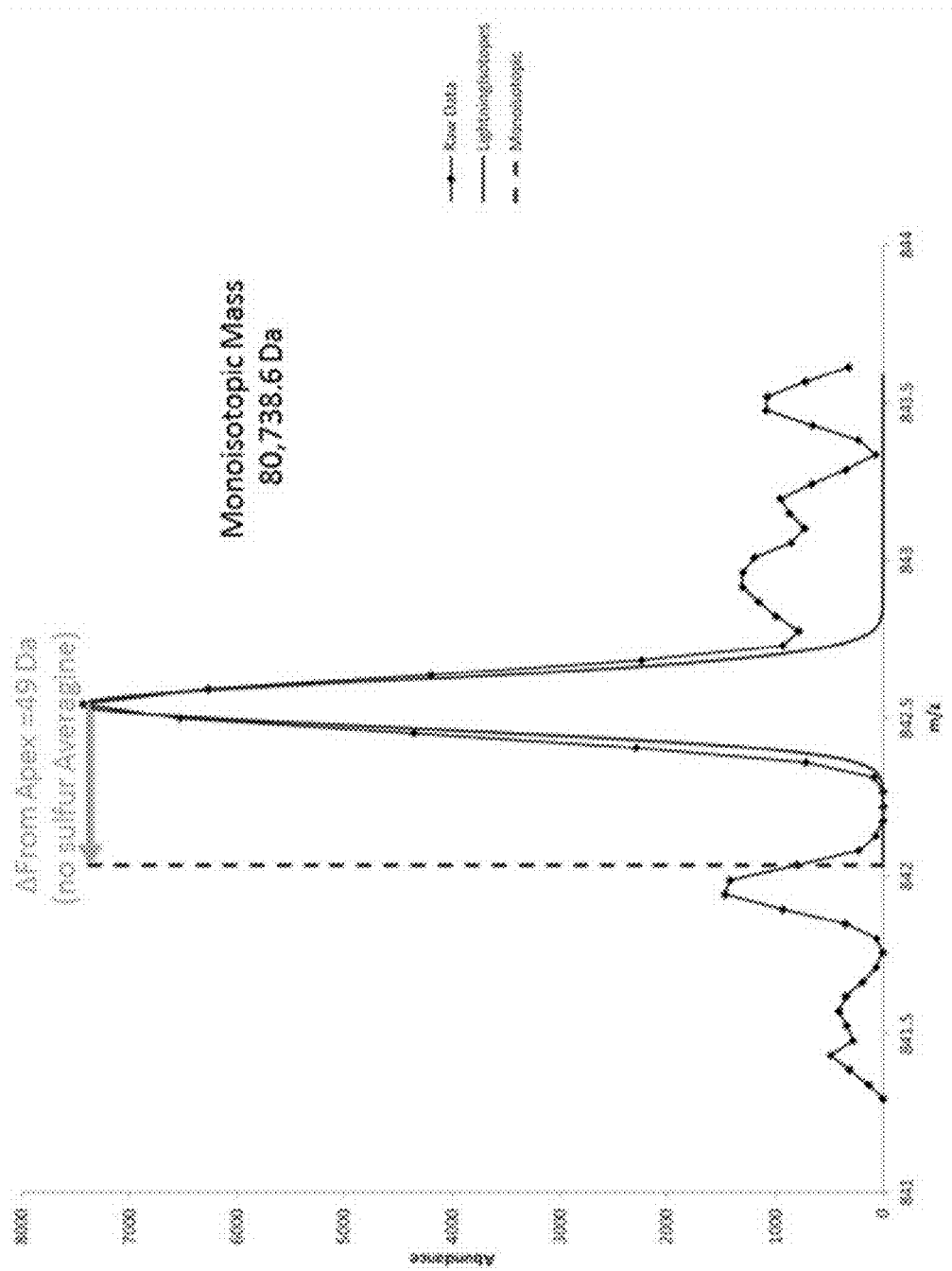
FIG. 12 is a simplified graphical representation of one embodiment of a mass calculation using the best fitting unresolved sample isotope profile to a reference isotope profile model.

FIG. 12 provides another illustrative example of an accurate mass calculation using the best fitting unresolved sample isotope profile to a reference isotope profile model. Using the best fit isotopic profile and a known model apex-to-monoisotopic mass delta of 49 Da, the monoisotopic mass value of the protein is about 80,738.6 Da. The raw data is represented as the dotted line, the best fit model isotope profile is illustrated as the solid line, and the position of the monoisotopic mass value is represented as the vertical dashed line. In the present example, the sample isotope profile does not include representations of individual isotope centroids so the geometric peak of the sample isotope profile was fit to the geometric centroid of the reference isotope profile model using the approximate monoisotopic mass value of the sample isotope profile to identify the appropriate reference isotope profile model.

In the embodiments described herein, interpretation application 220 identifies the material that corresponds to the monoisotopic mass value and best fitting reference model, illustrated in FIG. 2 as material data 245, which is provided to user 101 via computer 110.

Having described various embodiments and implementations, it should be apparent to those skilled in the relevant art that the foregoing is illustrative only and not limiting, having been presented by way of example only. Many other schemes for distributing functions among the various functional elements of the illustrated embodiments are possible. The functions of any element may be carried out in various ways in alternative embodiments.

What is claimed is:

1. A method for calculating a mass value of a material, comprising:
   determining an approximate mass value for an unknown material from spectral information derived from mass spectral analysis of the unknown material;
   retrieving a plurality of profile models that correspond to a known material from a data structure using the approximate mass value;
   fitting a sample profile for the unknown material from the spectral information to the profile models to generate a fit score for each fit, wherein the lowest fit score corresponds to the best fit;
   calculating a mass value from the best fitting profile model and the sample profile.

2. The method of claim 1, further comprising: determining the known material corresponding to the best fitting profile model.

3. The method of claim 2, further comprising: calculating a measure of abundance of the known material.

4. The method of claim 3, wherein: the measure of abundance is calculated by scaling the sample profile by an intensity correction factor.

5. The method of claim 4, wherein: the intensity correction factor relationship is calculated using an apex isotope intensity as a divisor of a dividend comprising the sample profile scaled to the apex isotope intensity.

6. The method of claim 4, wherein: the intensity correction factor relationship is calculated using a floating filter area of an isotope profile as a devisor of a dividend comprising the sample profile scaled to the floating filter area of the isotope profile.

7. The method of claim 1, wherein: the data structure comprises a hash table.

8. The method of claim 7, wherein: the approximate mass value comprises a key value used to access the profile models in the hash table.

9. The method of claim 7, further comprising: retrieving an iteration table from the hash table data structure; and fitting the sample profile for the unknown material to the profile models using the iteration table.

10. The method of claim 9, wherein: the iteration table is pre-computed based on isotope information corresponding to the known material.

11. The method of claim 1, wherein: the approximate mass value comprises a monoisotopic mass value.

12. The method of claim 1, wherein: the approximate mass value comprises an average mass value.

13. The method of claim 1, wherein: the approximate mass value of the unknown material corresponds to a mass value of the known material.

14. The method of claim 1, wherein: the mass value is calculated using a data consolidation method of a plurality of mass values each corresponding to an isotope centroid from the sample profile.

15. The method of claim 14, wherein: the data consolidation method comprises an average.

16. The method of claim 14, wherein: the isotope centroids from the sample profile correspond to the plurality of mass values selected using a floating filter.

17. The method of claim 1, wherein: the profile models comprise a full isotope profile model corresponding to the known material reduced in size using a floating filter.

18. The method of claim 17, wherein: the floating filter defines a percentage range for the profile model centered on the peak of the profile model.

19. The method of claim 1, wherein: the steps of determining through calculating are performed in about 10 μs.

20. The method of claim 1, wherein: The sample profile comprises a single isotope profile corresponding to the unknown material.

21. The method of claim 1, wherein: The sample profile comprises an average from a plurality of isotope profiles corresponding to the unknown material.

22. The method of claim 1, further comprising: returning the mass value and the best fitting profile model to a user.

23. A system for calculating a mass value of a material, comprising:
    a mass spectrometer adapted to generate spectral information from an unknown material; and
    a computer having executable code stored thereon, wherein the executable code performs a method comprising:
        determining an approximate mass value for the unknown material from the spectral information;
        retrieving a plurality of profile models that correspond to a known material from a data structure using the approximate mass value;
        fitting a sample profile for the unknown material from the spectral information to the profile models to generate a fit score for each fit, wherein the lowest fit score corresponds to the best fit; and
        calculating a mass value from the best fitting profile model and the sample profile.

24. The system of claim 23, wherein the method performed by the executable code further comprises: determining the known material corresponding to the best fitting profile model.

25. The system of claim 24, wherein the method performed by the executable code further comprises: calculating a measure of abundance of the known material.

26. The system of claim 25, wherein: the measure of abundance is calculated by scaling the sample profile by an intensity correction factor.

27. The method of claim 26, wherein: the intensity correction factor relationship is calculated using an apex isotope intensity as a divisor of a dividend comprising the sample profile scaled to the apex isotope intensity.

28. The method of claim 26, wherein: the intensity correction factor relationship is calculated using a floating filter area of an isotope profile as a devisor of a dividend comprising the sample profile scaled to the floating filter area of the isotope profile.

29. The system of claim 23, wherein: the data structure comprises a hash table.

30. The system of claim 29, wherein: the approximate mass value comprises a key value used to access the profile models in the hash table.

31. The system of claim 29, wherein the method performed by the executable code further comprises: retrieving an iteration table from the hash table data structure; and fitting the sample profile for the unknown material to the profile models using the iteration table.

32. The system of claim 31, wherein: the iteration table is pre-computed based on isotope information corresponding to the known material.

33. The system of claim 23, wherein: the approximate mass value comprises a monoisotopic mass value.

34. The system of claim 23, wherein: the approximate mass value comprises an average mass value.

35. The system of claim 23, wherein: the approximate mass value of the unknown material corresponds to a mass value of the known material.

36. The system of claim 23, wherein: the mass value is calculated using a data consolidation method of a plurality of mass values each corresponding to an isotope centroid from the sample profile.

37. The system of claim 36, wherein: the data consolidation method comprises an average.

38. The system of claim 36, wherein: the isotope centroids from the sample profile correspond to the plurality of mass values selected using a floating filter.

39. The system of claim 23, wherein: the profile models comprise a full isotope profile model corresponding to the known material reduced in size using a floating filter.

40. The system of claim 39, wherein: the floating filter defines a percentage range for the profile model centered on the peak of the profile model.

41. The system of claim 23, wherein: the steps of determining through calculating are performed in about 10 μs.

42. The system of claim 23, wherein: The sample profile comprises a single isotope profile corresponding to the unknown material.

43. The system of claim 23, wherein: The sample profile comprises an average from a plurality of isotope profiles corresponding to the unknown material.

44. The system of claim 23, wherein the method performed by the executable code further comprises: returning the mass value and the best fitting profile model to a user.

* * * * *